United States Patent
Joyce-Shaikh et al.

(10) Patent No.: US 9,284,377 B2
(45) Date of Patent: Mar. 15, 2016

(54) MDL-1 LIGAND

(71) Applicant: Merck Sharp & Dohme Corp., Rahway, NJ (US)

(72) Inventors: Barbara Joyce-Shaikh, San Jose, CA (US); Douglas C. Wilson, San Mateo, CA (US); Daniel J. Cua, Palo Alto, CA (US); Drake M. LaFace, Half Moon Bay, CA (US); Joseph H. Phillips, Palo Alto, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/744,706

(22) Filed: Jun. 19, 2015

(65) Prior Publication Data

US 2015/0368344 A1 Dec. 24, 2015

Related U.S. Application Data

(62) Division of application No. 14/346,202, filed as application No. PCT/US2012/055690 on Sep. 17, 2012, now abandoned.

(60) Provisional application No. 61/663,186, filed on Jun. 22, 2012, provisional application No. 61/538,530, filed on Sep. 23, 2011.

(51) Int. Cl.
*C07K 16/28* (2006.01)
*G01N 33/50* (2006.01)
*C07K 14/705* (2006.01)
*A61K 39/00* (2006.01)

(52) U.S. Cl.
CPC ......... *C07K 16/2851* (2013.01); *C07K 14/7056* (2013.01); *G01N 33/505* (2013.01); *A61K 2039/505* (2013.01); *C07K 2317/76* (2013.01); *C07K 2319/00* (2013.01); *G01N 2333/4724* (2013.01); *G01N 2440/14* (2013.01); *G01N 2500/02* (2013.01); *G01N 2500/10* (2013.01)

(58) Field of Classification Search
None
See application file for complete search history.

(56) References Cited

U.S. PATENT DOCUMENTS

| | | |
|---|---|---|
| 2004/0072725 A1 | 4/2004 | Yoneda et al. |
| 2009/0004259 A1 | 1/2009 | Rabinovich et al. |
| 2010/0028418 A1 | 2/2010 | Van Vliet et al. |
| 2010/0129374 A1 | 5/2010 | Bakker et al. |
| 2010/0221252 A1 | 9/2010 | Bigler et al. |

FOREIGN PATENT DOCUMENTS

WO 9906557 A1 2/1999

OTHER PUBLICATIONS

Bakker, et al. (1999) Proc. Natl. Acad. Sci. USA 96(17):9792-9796"Myeloid DAP12-associating lectin (MDL)-1 is a cell surface receptor involved in the activation of myeloid cells."
Bi, et al (2011) Proc. Natl. Acad. Sci. USA 108(26):10650-10655"Galectin-9 binding to cell surface protein disulfide isomerase regulates the redox environment to enhance T-cell migration and HIV entry."
Blasius, et al. (2006) Blood 107(6):2474-2476, abstract."Siglec-H is an IPC-specific receptor that modulates type I IFN secretion through DAP12."
Buonocore, et al. (2010) Nature 464:1371-1375, abstract"Innate lymphoid cells drive interleukin-23-dependent innate intestinal pathology."
Chen, et al. (2008) Nature 453(7195):672-676 "CLEC5A is critical for dengue-virus-induced lethal disease."
Chou, et al. (2009) Eur. J. Immunol. 39(9):2403-2411"Attenuation of Th1 response through galectin-9 and T-cellIg mucin 3 interaction inhibits autoimmune diabetes in NOD mice."
International Search Report for PCT/US12/55690 dated Feb. 7, 2013.
Dardalhon, et al. (2010) J Immunol. 185(3):1383-1392"Tim-3/galectin-9 pathway: regulation of Th1 immunity through promotion of CD11b+Ly-6G+ myeloid cells."
Fulcher, et al. (2009) J Biol Chem 284(39):26860-26870, abstract"Galectin-1 co-clusters CD43/CD45 on dendritic cells and induces cell activation and migration through Syk and protein kinase C signaling."
GenBank Accession No. AAN21593 (Sep. 25, 2002).
GenBank Accession No. AR217548 (Sep. 25, 2002).
GenBank Accession No. AR217549 (Sep. 25, 2002).
Jayaraman et al. (2010) J. Exp Med. 207(11):2343-2354"Tim3 binding to galectin-9 stimulates antimicrobial immunity."
Joyce-Shaikh, et al., Myeloid DAP12-associating lectin (MDL)-1 regulates synovial inflammation and bone erosion associated with autoimmune arthritis, 2010, 579-589, 207-3, J. Exp. Med.
NCBI Accession No. NP_002299 (May 5, 2014).
NCBI Accession No. NP_033665 (May 5, 2014).
Niki, et al. (2009) J. Biol. Chem. 284(47):32344-32352"Galectin-9 is a high affinity IgE-binding lectin with anti-allergic effect by blocking IgE-antigen complex formation."
Nochi, et al. (2003) Am. J. of Pathology 162(4):1191-1201"Modulation of hepatic granulomatous responses by transgene expression of DAP12 or TREM-1-1g molecules."
Watson, et al. (2011) J. Biol. Chem. 286(27):24208-24218"Structural flexibility of the macrophage dengue virus receptor CLEC5A: implications for ligand binding and signaling."
Zhu, et al. (2005) Nat. Immunol. 6(12):1245-1252"The Tim-3 ligand galectin-9 negatively regulates T helper type 1 immunity."

*Primary Examiner* — Jacob Cheu
(74) *Attorney, Agent, or Firm* — Immac J. Thampoe; Li Su

(57) ABSTRACT

The invention provides methods for modulation interactions between MDL-1 and its binding partner, Gal9. Also provided are methods to screen for modulators of MDL-1/Gal9 interaction.

5 Claims, 4 Drawing Sheets

MDL-1 LIGAND

FIELD OF THE INVENTION

The present invention provides the binding partner of MDL-1, MDL-1 ligand compositions of matter and uses

BACKGROUND OF THE INVENTION

The control of unwanted immune responses is a critical issue in the treatment of diseases such as inflammation, autoimmune diseases, transplant rejection, allergic diseases, and some cancers. The activity of overly aggressive T cells can be controlled by immunosuppression or by the induction of immunological tolerance. Tolerance is defined as a state where the immune system is made unresponsive to an antigen, whereas immunosuppression, which decreases the immune response to antigens, usually requires the continued use of medication. In inflammation and autoimmune diseases, T cells play an essential role in the prolonged immune response to a certain stimulus. Current immunosuppressive regimes commonly involve the use of corticosteroid, cyclosporin or rapamycin, which block the transcription of IL-2, a key growth factor for T cells, or inhibit IL-2 dependent proliferation. However, a number of monoclonal antibodies that act as T cell-depleting agents (e.g. CD3, CD4, CD8), or as inhibitors of the cytokine signaling or the co-stimulatory pathways of T cells (e.g. CD25, B7-1, B7-2, CD152, CTLA4) have demonstrated effectiveness in reducing the incidence of rejection with limited side effects or toxicity. Some of these agents have been shown to have some degree of success in treating inflammatory and autoimmune diseases and in prolonging graft survival.

The myeloid receptor of the C-type lectin superfamily associated with DAP12 is Myeloid DAP12-associating Lectin-1 (MDL-1), a type II transmembrane protein (MDL-1 is also referred to as CLEC5a). MDL-1 was the first DAP12 associating molecule to be identified and cloned (Bakker et al. (1999) *PNAS USA* 96(17):9792-9796). It is expressed exclusively in myeloid cells (Bakker et al. (1999) *PNAS U.S.A.* 96:9792-9796) as well as on other myeloid cell types such as, neutrophils and dendritic cells. The presence of a negatively charged residue in the transmembrane domain of DAP12 precludes its cell surface expression in the absence of a partner receptor, such as MDL-1, which has a positively charged residue in its transmembrane domain. However, DAP12 alone is not sufficient for its expression and function at the cell surface. Thus, the combination of a DAP12-associating molecule, such as MDL-1, and DAP12 may account for transmitting a particular physiological signal via DAP12 (Nochi et al. (2003) *Am. J. of Pathology* 162:1191-1201).

MDL-1 has been found to possibly be the receptor for Dengue Virus on myeloid cells (see, e.g., Chen, et al. (2008) *Nature* 453:672-676). Recently, MDL-1 has been structurally characterized as a "C-type lectin-like" homodimeric molecule that is capable of conformational switching in the presence of Dengue Virus binding (see, e.g., Watson, et al. (2011) *J. Biol. Chem.* 286:24208-24218).

The present invention identifies a population of T lymphocyte cells that appear to express a protein involved in MDL-1 engagement and activation. The ligand appears to be a cell surface protein that may not directly interact with MDL-1, but rather involves a third protein. A sub-population of these cells also expresses IL-23 receptor (IL-23R). Upon activation by IL-23, these IL-23R$^+$, MDL-1L$^+$ expressing cells have been implicated in the progression of inflammation, in particular enthesopathy.

The non-viral binding partner of MDL-1, MDL-1 ligand ("MDL-1L"), is now identified as Galectin9 ("Gal9"). Galectin-9 (Gal-9) is a member of animal lectins that have an affinity to β-galactosides. Gal9 has been shown to bind to several other molecules, including T cell immunoglobulin and mucin domain-containing molecule ("TIM3"), which is expressed on Th1/Th17 cells, and is a negative regulator of Th1 immunity (see, e.g., Zhu, et al. (2005) *Nat. Immunol.* 6:1245-1252; and Jayaraman et al. (2010) *J. Exp Med.* 207: 2343-2354). Gal9 has also been shown to bind to other cell surface molecules such as CD44 and IgE (Niki, et al. (2009) *J. Biol. Chem.* 284:32344-32352), as well as protein disulfide isomerase (see, e.g., Bi, et al. (2011) *Proc. Natl. Acad. Sci.* 108:10650-10655).

Engagement MDL-1 by the Gal9 results in the activation of myeloid lineage cells (e.g., macrophages, osteoclasts) via DAP12, resulting in tyrosine phosphorylation of DAP12 and induction of an innate immune pathway. Uncontrolled induction of this pathway can either lead to chronic inflammation or improper clearance of infectious microbes. Thus a need exists to control the Gal9/MDL-1 interaction. The present invention provides methods to regulate this protein-protein interaction and screens to isolate additional regulatory compositions which modulate with this interaction.

SUMMARY OF THE INVENTION

Figure 1:
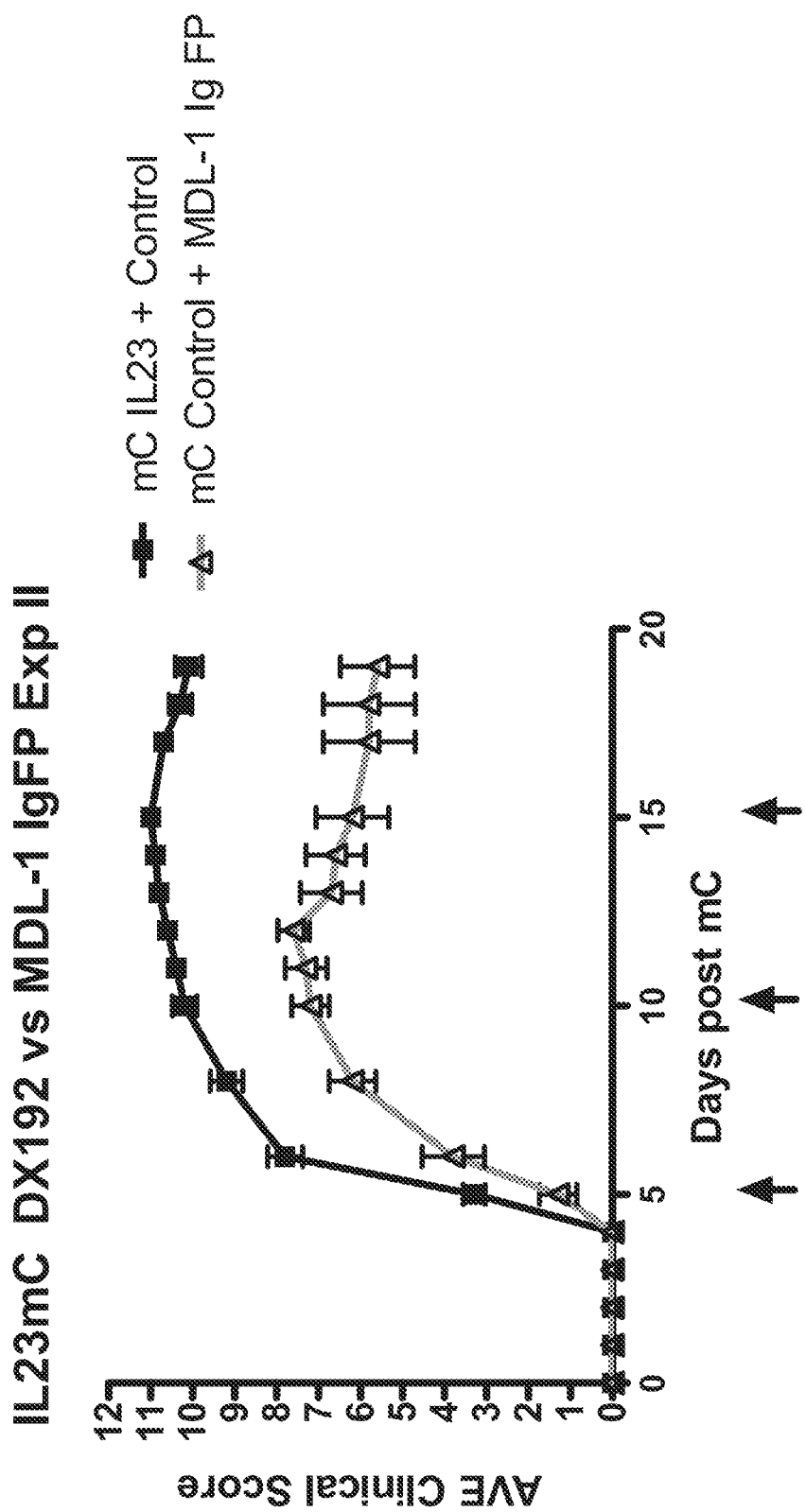
FIG. 1 shows that MDL-1-Ig can inhibit IL-23 induced enthesopathy. DX192 is an MDL-1 agonist antibody.

The present invention is based, in part, upon the discovery that Galectin-9 interacts with MDL-1, induces tyrosine phosphorylation of DAP-12 and stimulates MDL-1 activity on myeloid lineage cells. Further, the present invention identifies a selected population of T lymphocytes that express a membrane bound protein that binds to Gal9 and through Gal9, engages and modulates MDL-1 activity.

The present invention provides a method of modulating an interaction between a lectin-like molecule expressed on a myeloid cell and a lectin which binds to a receptor expressed by a T cell, comprising: a) providing a compound that is capable of binding to the lectin-like molecule at a binding site of the lectin; and b) presenting the compound of step (i) to the lectin-like molecule and the lectin and thereby modulating the interaction between the lectin-like molecule and the lectin. In certain embodiments, the lectin-like molecule is MDL-1 and the lectin is Gal9 In a further embodiment, the compound is an antibody or a binding fragment of an antibody, or a soluble receptor-Ig fusion protein that modulates the interaction between the lectin-like molecule and the lectin. The antibody binds MDL-1 and prevents the interaction of MDL-1 with Gal9.

The present invention also provides a method of screening for a compound that modulates an interaction between a lectin-like molecule expressed on myeloid cells, and a lectin which binds to a receptor expressed by a T cell, comprising: a) providing a compound that is capable of binding to the lectin-like molecule at a binding site of the lectin; and b) presenting the compound of step (a) to the lectin-like molecule and the lectin and thereby modulating the interaction between the lectin-like molecule and the lectin. In certain embodiments, the lectin-like molecule is MDL-1 and the lectin is Gal9. In another embodiment, the compound is an antibody or a binding fragment of an antibody. The antibody or binding fragment of an antibody inhibits the interaction of the lectin-like molecule with the lectin. In a further embodiment, the antibody or binding fragment of the antibody inhibits phosphorylation of a signaling molecule associated with the lectin-like molecule. In a further embodiment, the signaling molecule is DAP12 or Syk and the phosphorylation is tyrosine phosphorylation.

The present invention provides A method of depleting a population of T lymphocyte cells comprising contacting the population of T lymphocyte cells with an MDL-1 fusion protein that binds directly or indirectly to a molecule expressed on the T lymphocyte cells. In one embodiment, the MDL-1 fusion protein comprises an extracellular domain of MDL-1 and a heterologous protein. The heterologous protein can be an Fc portion of an immunoglobulin molecule or human serum albumin. In certain embodiments, the population of T lymphocyte cells express CD45, CD90, and CD117. Additionally the population of T lymphocyte cells can express IL-23R, which mediates enthesopathy.

DETAILED DESCRIPTION

As used herein, including the appended claims, the singular forms of words such as "a," "an," and "the," include their corresponding plural references unless the context clearly dictates otherwise.

All references cited herein are incorporated by reference to the same extent as if each individual publication, patent application, or patent, was specifically and individually indicated to be incorporated by reference.

DEFINITIONS

"Activity" of a molecule may describe or refer to the binding of the molecule to a ligand or to a receptor, to catalytic activity, to the ability to stimulate gene expression, to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" may also mean specific activity, e.g., [catalytic activity]/[mg protein], or [immunological activity]/[mg protein], or the like.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, and in U.S. patent application Ser. Nos. 09/801,185 and 10/302,356, each of which is incorporated herein by reference in its entirety.

The term "antigen-binding portion" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). The antibody portions of the invention are described in further detail in U.S. Pat. Nos. 6,090,382, 6,258,562, 6,509,015, and in U.S. patent application Ser. Nos. 09/801,185 and 10/302,356, each of which is incorporated herein by reference in its entirety.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), betabranched side chains (e.g., threonine, valine, isoleucine) and aromatic side chains (e.g., tyrosine, phenylalanine, tryptophan, histidine).

As used herein, the term "anti-idiotypic antibodies" or "anti-idiotypes" refers to antibodies directed against the antigen-combining region or variable region (called the idiotype) of another antibody molecule. As disclosed by Jerne et al. (Jerne, N. K., (1974) *Ann. Immunol.* (Paris) 125c:373 and Jerne, N. K., et al., (1982) *EMBO* 1:234), immunization with an antibody molecule expressing a paratope (antigen-combining site) for a given antigen (e.g., an MDL-1 peptide) will produce a group of anti-antibodies, some of which share, with the antigen, a complementary structure to the paratope. Immunization with a subpopulation of the anti-idiotypic antibodies will, in turn, produce a subpopulation of antibodies or immune cell subsets that are reactive to the initial antigen.

As used herein, the term "fully human antibody" refers to an antibody which comprises human immunoglobulin protein sequences only. A fully human antibody may contain murine carbohydrate chains if produced in a mouse, in a mouse cell or in a hybridoma derived from a mouse cell. Similarly, "mouse antibody" refers to an antibody which comprises mouse immunoglobulin sequences only.

"Humanized" antibodies are also within the scope of the present invention. As used herein, the term "humanized" or "fully humanized" refers to an antibody that contains the amino acid sequences from the six complementarity-determining regions (CDRs) of the parent antibody, e.g., a mouse antibody, grafted to a human antibody framework. Humanized forms of non-human (e.g., murine or chicken) antibodies are chimeric immunoglobulins, which contain minimal sequence derived from non-human immunoglobulin. For the most part, humanized antibodies are human immunoglobulins (recipient antibody) in which residues from a complementary determining region of the recipient are replaced by residues from a complementary determining region of a non-human species (donor antibody), such as mouse, chicken, rat or rabbit, having a desired specificity, affinity and capacity. In some instances, Fv framework residues of the human immunoglobulin are also replaced by corresponding non-human residues.

As used herein, the term "partially humanized" or "chimeric" antibody means an antibody that contains heavy and light chain variable regions of, e.g., murine origin, joined onto human heavy and light chain constant regions.

An alternative to humanization is to use human antibody libraries displayed on phage or human antibody libraries contained in transgenic mice, see, e.g., Vaughan et al. (1996) *Nat. Biotechnol.* 14:309-314; Barbas (1995) *Nature Med.* 1:837-839; de Haard et al. (1999) *J. Biol. Chem.* 274:18218-18230; McCafferty et al. (1990) *Nature* 348:552-554; Clackson et al. (1991) *Nature* 352:624-628; Marks et al. (1991) *J. Mol. Biol.* 222:581-597; Mendez et al. (1997) *Nature Genet.* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nat. Biotechnol.* 17:397-399.

As used herein, the term "human" refers to antibodies containing amino acid sequences that are of 100% human origin, where the antibodies may be expressed, e.g., in a human, animal, insect, fungal, plant, bacterial, or viral host (Baca et al. (1997) *J. Biol. Chem.* 272:10678-10684; Clark (2000) *Immunol. Today* 21:397-402).

The present invention includes "chimeric antibody" which means an antibody that comprises a variable region of the present invention fused or chimerized with an antibody region (e.g., constant region) from another, non-human species (e.g., mouse, horse, rabbit, dog, cow, chicken). These antibodies may be used to modulate the expression or activity of MDL-1 in the non-human species.

As used herein, the term "human/mouse chimeric antibody" refers to an antibody which comprises a mouse variable region ($V_H$ and $V_L$) fused to a human constant region.

As used herein, the term "single-chain Fv" or "sFv" antibody fragments means antibody fragment that have the $V_H$ and $V_L$ domains of an antibody, wherein these domains are present in a single polypeptide chain. Generally, the sFv polypeptide further comprises a polypeptide linker between the $V_H$ and $V_L$ domains which enables the sFv to form the desired structure for antigen binding. Techniques described for the production of single chain antibodies (U.S. Pat. Nos. 5,476,786, 5,132,405 and 4,946,778) may be adapted to produce anti-MDL-1L-specific single chain antibodies. For a review of sFv see Pluckthun in *The Pharmacology of Monoclonal Antibodies*, vol. 113, Rosenburg and Moore eds. Springer-Verlag, N.Y., pp. 269-315 (1994).

Single chain antibodies, single domain antibodies, and bispecific antibodies are described, see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290, Kostelney et al. (1992) *J. Immunol.* 148:1547-1553; U.S. Pat. Nos. 5,932,448; 5,532,210; 6,129,914; 6,133,426; 4,946,778.

As used herein, the terms "disulfide stabilized Fv fragments" and "dsFv" refer to antibody molecules comprising a variable heavy chain ($V_H$) and a variable light chain ($V_L$) which are linked by a disulfide bridge.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor, L. D., et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody", as used herein, is intended to refer to an antibody that is substantially free of other antibodies having different antigenic specificities (e.g., an isolated antibody that specifically binds MDL-1 is substantially free of antibodies that specifically bind antigens other than MDL-1). An isolated antibody that specifically binds MDL-1 may, however, have cross-reactivity to other antigens, such as MDL-1 molecules from other species (discussed in further detail below). Moreover, an isolated antibody may be substantially free of other cellular material and/or chemicals.

The term "multivalent antibody" refers to an antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" or "dual specific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope A "neutralizing antibody", as used herein (or an "antibody that neutralized hTNFα activity"), is intended to refer to an antibody whose binding to MDL-1 results in inhibition of the biological activity of MDL-1. This inhibition of the biological activity of MDL-1 can be assessed by measuring one or more indicators of MDL-1 biological activity, such as MDL-1 induced cytotoxicity (either in vitro or in vivo), MDL-1-induced cellular activation and MDL-1 binding to Gal9. These indicators of MDL-1 biological activity can be assessed by one or more of several standard in vitro or in vivo assays known in the art.

The term "antigen-binding portion" or "antigen-binding fragment" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Binding fragments include Fab, Fab', F(ab')$_2$, Fabc, Fv, single chains, and single-chain antibodies. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH or VL domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 and Joensson, U., et al. (1993) *Ann. Biol. Clin.* 51:19-26; Joensson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., VH, VL, CDR3) that bind MDL-1 is intended to refer to a nucleic acid molecule in which the nucleotide sequences encoding the antibody or antibody portion are free of other nucleotide sequences encoding antibodies or antibody portions that bind antigens other than MDL-1, which other sequences may naturally flank the nucleic acid in human genomic DNA. Thus, for example, an isolated nucleic acid of the invention encoding a VH region of an anti-MDL-1L antibody contains no other sequences encoding other VH regions that bind antigens other than MDL-1.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "kit" as used herein refers to a packaged product comprising components with which to administer the anti-MDL-1 antibodies of the invention for treatment of a MDL-1 related disorder. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering the anti-MDL-1 antibodies or MDL-1 soluble fusion protein of the invention, e.g., an Ig-MDL-1 fusion.

MDL-1

The invention is directed to methods of modulating myeloid cell activity by modulating the function of the MDL-1, also known as C-type lectin superfamily member 5 (CLECSF5), molecules residing on the surface of a myeloid cell, in particular a macrophage, including osteoblasts and osteoclasts. Engagement of MDL-1 with Gal9 herein can also cause the activation of macrophage cells and the induction of inflammation. The ability to modulate the MDL-1/Gal9 interaction will allow control of myeloid inflammation.

The terms "MDL-1", "Myeloid DAP12 associating lectin-1", "Myeloid DAP12-associated lectin-1", "DAP-12", "DAP12", "DNAX Activation Protein, 12 kD" are well known in the art. The human and mouse DAP12 and MDL-1 nucleotide and polypeptide sequences are disclosed in WO 99/06557. GenBank® deposits of the human MDL-1 nucleic acid sequence (AR217548) and mouse MDL-1 nucleic and amino acid sequences (AR217549 and AAN21593, respectively) are also available.

The terms "Galectin9", "Gal9", "T cell Immunoglobulin Mucin", and "Tim3" are well known in the art. Polypeptide sequences of human Gal9 are provided in GenBank® deposits NP_002299 (short form) and NP 033665 (long form).

A structural feature of the MDL-1 protein is the extracellular domain, which is defined by amino acid residues 26 to 188 of the human MDL-1 protein, and amino acid residues 26 to 190 of the mouse MDL-1 protein. Soluble MDL-1 protein can be fused to heterologous proteins, e.g., the Fc portion of an immunoglobulin molecule, or conjugated to chemical moieties, e.g., PEG, human serum albumin.

Soluble MLD-1 proteins alone or in combination with heterologous proteins can be used to deplete a population of T lymphocytes. These T lymphocytes can express certain cell surface molecules including CD45, CD90, and CD117. Additionally, IL-23R can also be expressed by the T lymphocyte population. Expression of IL-23R allows these cells to mediate enthesopathy.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); Transcription And Translation (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

The sequence of any nucleic acid (e.g., a nucleic acid encoding an antibody that modulates the MDL-1/Gal9 interaction) may be sequenced by any method known in the art (e.g., chemical sequencing or enzymatic sequencing). "Chemical sequencing" of DNA may denote methods such as that of Maxam and Gilbert (1977) (*Proc. Natl. Acad. Sci. USA* 74:560), in which DNA is randomly cleaved using individual base-specific reactions. "Enzymatic sequencing" of DNA may denote methods such as that of Sanger (Sanger et al., (1977) *Proc. Natl. Acad. Sci. USA* 74:5463).

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

Promoters, which may be used to control gene expression, include, but are not limited to, the cytomegalovirus (CMV) promoter (U.S. Pat. Nos. 5,385,839 and 5,168,062), the SV40 early promoter region (Benoist et al., (1981) *Nature* 290:304-310), the promoter contained in the 3' long terminal repeat of Rous sarcoma virus (Yamamoto et al., (1980) *Cell* 22:787-797), the herpes thymidine kinase promoter (Wagner et al., (1981) *Proc. Natl. Acad. Sci. USA* 78:1441-1445), the regulatory sequences of the metallothionein gene (Brinster et al., (1982) *Nature* 296:39-42); prokaryotic expression vectors such as the β-lactamase promoter (Villa-Komaroff et al., (1978) *Proc. Natl. Acad. Sci. USA* 75:3727-3731), or the tac promoter (DeBoer et al., (1983) *Proc. Natl. Acad. Sci. USA* 80:21-25); see also "Useful proteins from recombinant bacteria" in *Scientific American* (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be trans-RNA spliced (if it contains introns) and, optionally, translated into a protein encoded by the coding sequence.

The present invention contemplates modifications, especially any superficial or slight modification, to the amino acid or nucleotide sequences that correspond to the proteins. In particular, the present invention contemplates sequence conservative variants of the nucleic acids that encode the human MDL-1 and mouse MDL-1 of the invention.

A nucleic acid molecule is "hybridizable" to another nucleic acid molecule, such as a cDNA, genomic DNA, or RNA, when a single stranded form of the nucleic acid molecule may anneal to the other nucleic acid molecule under the appropriate conditions of temperature and solution ionic strength (see Sambrook et al., supra). The conditions of temperature and ionic strength determine the "stringency" of the hybridization. Typical low stringency hybridization conditions may be 55° C., 5×SSC, 0.1% SDS, 0.25% milk, and no formamide; or 30% formamide, 5×SSC, 0.5% SDS. Typical, moderate stringency hybridization conditions are similar to the low stringency conditions except the hybridization is carried out in 40% formamide, with 5× or 6×SSC. High stringency hybridization conditions are similar to low stringency conditions except the hybridization conditions are carried out in 50% formamide, 5× or 6×SSC and, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook, et al., supra, 11.7-11.8).

Also included in the present invention are nucleic acids comprising nucleotide sequences and polypeptides comprising amino acid sequences that are at least 70% identical, at least 80% identical, at least 90% identical e.g., 91%, 92%, 93%, 94%, and at least 95% identical e.g., 95%, 96%, 97%, 98%, 99%, 100%, to the reference nucleotide and amino acid sequences of Table 1 when the comparison is performed by a BLAST algorithm wherein the parameters of the algorithm are selected to give the largest match between the respective sequences over the entire length of the respective reference sequences. Polypeptides comprising amino acid sequences which are at least 70% similar, at least 80% similar, at least 90% similar e.g., 91%, 92%, 93%, 94%, and at least 95% similar e.g., 95%, 96%, 97%, 98%, 99%, 100%, to the reference amino acid sequences of Table 1 e.g., SEQ ID NOs: 2 and 4, when the comparison is performed with a BLAST algorithm wherein the parameters of the algorithm are selected to give the largest match between the respective sequences over the entire length of the respective reference sequences, are also included in the present invention.

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithm are herein incorporated by reference: BLAST ALGORITHMS: Altschul et al., (1990) J. Mol. Biol. 215:403-410; Gish et al., (1993) Nature Genet. 3:266-272; Madden et al., (1996) Meth. Enzymol. 266:131-141; Altschul et al., (1997) Nucleic Acids Res. 25:3389-3402; Zhang et al., (1997) Genome Res. 7:649-656; Wootton et al., (1993) Comput. Chem. 17:149-163; Hancock et al., (1994) Comput. Appl. Biosci. 10:67-70; ALIGNMENT SCORING SYSTEMS: Dayhoff et al., "A model of evolutionary change in proteins." in *Atlas of Protein Sequence and Structure*, (1978) vol. 5, suppl. 3, M. O. Dayhoff (ed.), pp. 345-352, Natl. Biomed. Res. Found., Washington, D.C.; Schwartz et al., "Matrices for detecting distant relationships." in *Atlas of Protein Sequence and Structure*, (1978) vol. 5, suppl. 3, M. O. Dayhoff (ed.), pp. 353-358, Natl. Biomed. Res. Found., Washington, D.C.; Altschul (1991) J. Mol. Biol. 219:555-565; States et al., (1991) Methods 3:66-70; Henikoff et al., (1992) Proc. Natl. Acad. Sci. USA 89:10915-10919; Altschul et al., (1993) J. Mol. Evol. 36:290-300; ALIGNMENT STATISTICS: Karlin et al., (1990) Proc. Natl. Acad. Sci. USA 87:2264-2268; Karlin et al., (1993) Proc. Natl. Acad. Sci. USA 90:5873-5877; Dembo et al., (1994) Ann. Prob. 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, N.Y.

The present invention also includes recombinant versions of the soluble form of MDL-1 that bind to MDL-1. Soluble versions can include Ig-MDL-1, Fc-MDL-1, and human serum albumin-MDL-1 fusion proteins. Soluble molecules can also be multimeric forms of MDL-1, e.g., tetramers. Moreover, fragments of the extracellular domain will also provide soluble forms of the MDL-1 protein. Fragments can be prepared using known techniques to isolate a desired portion of the extracellular region.

Conventional molecular biology techniques can be used to produce chimeric proteins having MDL-1 fused a heterologous enzymatically inactive polypeptide (e.g., a lytic or non-lytic Fc region of IgG, human serum albumin). Numerous polypeptides are suitable for use as enzymatically inactive proteins in the invention. Preferably, the protein has a molecular weight of at least 10 kD; a net neutral charge at pH 6.8; a globular tertiary structure; and of human origin. Where the enzymatically inactive polypeptide is IgG, preferably, the IgG portion is glycosylated. If desired, the enzymatically inactive polypeptide can include an IgG hinge region positioned such that the chimeric protein has MDL-1 bonded to an IgG hinge region with the hinge region bonded to a longevity-increasing polypeptide. Thus, the hinge region can serve as a spacer between the cytokine and the longevity-increasing polypeptide. A person skilled in molecular biology can readily produce such molecules from an IgG2a-secreting hybridoma (e.g., HB129) or other eukaryotic cells or baculovirus systems. As an alternative to using an IgG hinge region, a flexible polypeptide spacer, as defined herein, can be used. Using conventional molecular biology techniques, such a polypeptide can be inserted between MDL-1 and the longevity-increasing polypeptide.

Where the heterologous protein includes an Fc region, the Fc region can be mutated, if desired, to inhibit its ability to fix complement and bind the Fc receptor with high affinity. For murine IgG Fc, substitution of Ala residues for Glu 318, Lys 320, and Lys 322 renders the protein unable to direct ADCC. Substitution of Glu for Leu 235 inhibits the ability of the protein to bind the Fc receptor with high affinity. Appropriate mutations for human IgG also are known (see, e.g., Morrison et al., 1994, The Immunologist 2: 119-124 and Brekke et al., 1994, The Immunologist 2: 125). Other mutations can also be used to inhibit these activities of the protein, and art-recognized methods can be used to assay for the ability of the protein to fix complement or bind the Fc receptor. Other useful heterologous polypeptides include albumin (e.g., human serum albumin), transferrin, enzymes such as t-PA which have been inactivated by mutations, and other proteins with a long circulating half-life and without enzymatic activity in humans.

Preferably, the enzymatically inactive polypeptide used in the production of the chimeric protein (e.g., IgG Fc) has, by itself, an in vivo circulating half-life greater than that of the extracellular portion of the fusion partner alone (e.g., MDL-1). More preferably, the half-life of the chimeric protein is at least 2 times that of the cytokine alone. Most preferably, the half-life of the chimeric protein is at least 10 times that of the cytokine alone. The circulating half-life of the chimeric protein can be measured in an ELISA of a sample of serum obtained from a patient treated with the chimeric protein. In such an ELISA, antibodies directed against the cytokine can be used as the capture antibodies, and antibodies directed against the enzymatically inactive protein can be used as the detection antibodies, allowing detection of only the chimeric protein in a sample. Conventional methods for performing ELISAs can be used, and a detailed example of such an ELISA is provided herein.

The chimeric proteins can be synthesized (e.g., in mammalian cells) using conventional methods for protein expression using recombinant DNA technology. Because many of the polypeptides used to create the chimeric proteins have been previously purified, many of the previously-described methods of protein purification should be useful, along with other conventional methods, for purifying the chimeric proteins of the invention. If desired, the chimeric protein can be affinity-purified according to standard protocols with antibodies directed against the cytokine Antibodies directed against the enzymatically inactive protein are also useful for purifying the chimeric protein by conventional immunoaffinity techniques. If desired, the activity of the chimeric protein can be assayed with methods that are commonly used to test the activity of the protein alone. It is not necessary that the activity of the chimeric protein be identical to the activity of the protein alone.

The present invention also includes fusions which include the polypeptides and polynucleotides of the present invention and a second polypeptide or polynucleotide moiety, which may be referred to as a "tag". The fused polypeptides of the invention may be conveniently constructed, for example, by insertion of a polynucleotide of the invention or fragment thereof into an expression vector as described above. The fusions of the invention may include tags which facilitate purification or detection. Such tags include glutathione-S-transferase (GST), hexahistidine (His6) tags, maltose binding protein (MBP) tags, haemagglutinin (HA) tags, cellulose binding protein (CBP) tags and myc tags. Detectable labels or tags such as $^{32}P$, $^{35}S$, $^{14}C$, $^{3}H$, $^{99m}Tc$, $^{111}In$, $^{68}Ga$, $^{18}F$, $^{125}I$, $^{131}I$, $^{113m}In$, $^{76}Br$, $^{67}Ga$, $^{99m}Tc$, $^{123}I$, $^{111}In$ and $^{68}Ga$ may also be used to label the polypeptides of the invention. Methods for constructing and using such fusions are very conventional and well known in the art.

Modifications (e.g., post-translational modifications) that occur in a polypeptide often will be a function of how it is made. For polypeptides made by expressing a cloned gene in a host, for instance, the nature and extent of the modifications, in large part, will be determined by the host cell's post-translational modification capacity and the modification signals present in the polypeptide amino acid sequence. For instance, as is well known, glycosylation often does not occur in bacterial hosts such as E. coli. Accordingly, when glycosylation is desired, a polypeptide may be expressed in a glycosylating host, generally a eukaryotic cell. Insect cells often carry out post-translational glycosylations which are similar to those of mammalian cells. For this reason, insect cell expression systems have been developed to express, efficiently, mammalian proteins having native patterns of glycosylation. Alternatively, deglycosylation enzymes may be used to remove carbohydrates attached during production in eukaryotic expression systems.

Analogs of the MDL-1 peptides of the invention may be prepared by chemical synthesis or by using site-directed mutagenesis, Gillman et al., (1979) Gene 8:81; Roberts et al., (1987) Nature, 328:731 or Innis (Ed.), 1990, *PCR Protocols: A Guide to Methods and Applications*, Academic Press, New York, N.Y. or the polymerase chain reaction method PCR; Saiki et al., (1988) Science 239:487, as exemplified by Daugherty et al., (1991) (Nucleic Acids Res. 19:2471) to modify nucleic acids encoding the peptides. Adding epitope tags for purification or detection of recombinant products is envisioned.

Protein Purification

Typically, the peptides of the invention may be produced by expressing a nucleic acid which encodes the polypeptide in a host cell which is grown in a culture (e.g., liquid culture such as Luria broth). For example, the nucleic acid may be part of a vector (e.g., a plasmid) which is present in the host cell. Following expression, the peptides of the invention may be isolated from the cultured cells. The peptides of this invention may be purified by standard methods, including, but not limited to, salt or alcohol precipitation, affinity chromatography (e.g., used in conjunction with a purification tagged peptide as discussed above), preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are very well known in the art and are disclosed, e.g., in "Guide to Protein Purification", *Methods in Enzymology*, Vol. 182, M. Deutscher, Ed., 1990, Academic Press, New York, N.Y.

Antibody Structure

In general, the basic antibody structural unit is known to comprise a tetramer. Each tetramer includes two identical pairs of polypeptide chains, each pair having one "light" (about 25 kDa) and one "heavy" chain (about 50-70 kDa). The amino-terminal portion of each chain may include a variable region of about 100 to 110 or more amino acids primarily responsible for antigen recognition. The carboxy-terminal portion of each chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes).

The variable regions of each light/heavy chain pair may form the antibody binding site. Thus, in general, an intact IgG antibody has two binding sites. Except in bifunctional or bispecific antibodies, the two binding sites are, in general, the same.

Normally, the chains all exhibit the same general structure of relatively conserved framework regions (FR) joined by three hypervariable regions, also called complementarity determining regions or CDRs. The CDRs from the two chains of each pair are usually aligned by the framework regions, enabling binding to a specific epitope. In general, from N-terminal to C-terminal, both light and heavy chains comprise the domains FR1, CDR1, FR2, CDR2, FR3, CDR3 and FR4. The assignment of amino acids to each domain is, generally, in accordance with the definitions of *Sequences of Proteins of Immunological Interest*, Kabat et al.; National Institutes of Health, Bethesda, Md.; $5^{th}$ ed.; NIH Publ. No. 91-3242 (1991); Kabat (1978) *Adv. Prot. Chem.* 32:1-75; Kabat et al., (1977) *J. Biol. Chem.* 252:6609-6616; Chothia et al., (1987) *J Mol. Biol.* 196:901-917 or Chothia et al., (1989) *Nature* 342: 878-883.

Antibody Molecules

The anti-MDL-1 antibody molecules of the invention preferably recognize human MDL-1 at the site of Gal9 interaction or antagonize ligand signaling in another manner. In an embodiment, fully-human monoclonal antibodies directed against MDL-1 are generated using transgenic mice carrying parts of the human immune system rather than the mouse system. These transgenic mice, which may be referred to, herein, as "HuMAb" mice, contain a human immunoglobulin gene miniloci that encodes unrearranged human heavy (μ and γ) and κ light chain immunoglobulin sequences, together with targeted mutations that inactivate the endogenous μ and κ chain loci (Lonberg, N., et al., (1994) Nature 368(6474):856-859). These antibodies are also referred to as fully human antibodies. Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N., et al., (1994), supra; reviewed in Lonberg, N. (1994) *Handbook of Experimental Pharmacology* 113:49-101; Lonberg et al., (1995) *Intern. Rev. Immunol.* 13:65-93, and Harding et al., (1995) *Ann. N. Y Acad. Sci* 764:536-546). The preparation of HuMab mice is commonly known in the art and is described, for example, in Taylor et al., (1992) *Nucleic Acids Research* 20:6287-6295; Chen et al., (1993) *International Immunology* 5:647-656; Tuaillon et al., (1993) *Proc. Natl. Acad. Sci USA* 90:3720-3724; Choi et al., (1993) *Nature Genetics* 4:117-123; Chen et al., (1993) *EMBO J.* 12:821-830; Tuaillon et al., (1994) *J Immunol.* 152:2912-2920; Lonberg et al., (1994) *Nature* 368(6474):856-859; Lonberg, N. (1994) *Handbook of Experimental Pharmacology* 113:49-101; Taylor et al., (1994) *International Immunology* 6:579-591; Lonberg et al., (1995) *Intern. Rev. Immunol.* Vol. 13:65-93; Harding et al., (1995) *Ann. N.Y Acad. Sci* 764:536-546; Fishwild et al., (1996) *Nature Biotechnology* 14:845-851 and Harding et al., (1995) *Annals NY Acad. Sci.* 764:536-546; the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874, 299; 5,770,429 and 5,545,807; and International Patent Application Publication Nos. WO 98/24884; WO 94/25585; WO 93/12227; WO 92/22645 and WO 92/03918 the disclosures of all of which are hereby incorporated by reference in their entity.

To generate fully human, monoclonal antibodies to MDL-1, HuMab mice may be immunized with an antigenic MDL-1 polypeptide as described by Lonberg et al., (1994) *Nature* 368(6474):856-859; Fishwild et al., (1996) *Nature Biotechnology* 14:845-851 and WO 98/24884. Preferably, the mice will be 6-16 weeks of age upon the first immunization. For example, a purified preparation of MDL-1 may be used to immunize the HuMab mice intraperitoneally. The mice may also be immunized with whole cells which are stably transformed or transfected with an MDL-1 gene.

In general, HuMAb transgenic mice respond well when initially immunized intraperitoneally (IP) with antigen in complete Freund's adjuvant, followed by every other week IP immunizations (usually, up to a total of 6) with antigen in incomplete Freund's adjuvant. Mice may be immunized, first, with cells expressing MDL-1L, then with a soluble fragment of MDL-1 and continually receive alternating immunizations with the two antigens. The immune response may be monitored over the course of the immunization protocol with plasma samples being obtained by retroorbital bleeds. The plasma may be screened for the presence of anti-MDL-1 antibodies, for example by ELISA, and mice with sufficient titers of immunoglobulin may be used for fusions. Mice may be boosted intravenously with antigen 3 days before sacrifice and removal of the spleen. It is expected that 2-3 fusions for each antigen may need to be performed. Several mice may be immunized for each antigen. For example, a total of twelve HuMAb mice of the HC07 and HC012 strains may be immunized.

Hybridoma cells which produce the monoclonal anti-MDL-1 antibodies may be produced by methods which are commonly known in the art. These methods include, but are not limited to, the hybridoma technique originally developed by Kohler, et al., (1975) (*Nature* 256:495-497), as well as the trioma technique (Hering et al., (1988) *Biomed. Biochim. Acta.* 47:211-216 and Hagiwara et al., (1993) *Hum. Antibod. Hybridomas* 4:15), the human B-cell hybridoma technique (Kozbor et al., (1983) *Immunology Today* 4:72 and Cote et al., (1983) *Proc. Natl. Acad. Sci. U.S.A* 80:2026-2030), and the EBV-hybridoma technique (Cole et al., in *Monoclonal Antibodies and Cancer Therapy*, Alan R. Liss, Inc., pp. 77-96, 1985). Preferably, mouse splenocytes are isolated and fused with PEG to a mouse myeloma cell line based upon standard protocols. The resulting hybridomas may then be screened for the production of antigen-specific antibodies. For example, single cell suspensions of splenic lymphocytes from immunized mice may by fused to one-sixth the number of P3X63-Ag8.653 nonsecreting mouse myeloma cells (ATCC, CRL 1580) with 50% PEG. Cells may be plated at approximately 2×10⁵ cells/mL in a flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells may be cultured in medium in which the HAT is replaced with HT. Individual wells may then be screened by ELISA for human anti-MDL-1 monoclonal IgG antibodies. Once extensive hybridoma growth occurs, medium may be observed usually after 10-14 days. The antibody secreting hybridomas may be replated, screened again, and if still positive for human IgG, anti-MDL-1 monoclonal antibodies, may be subcloned at least twice by limiting dilution. The stable subclones may then be cultured in vitro to generate small amounts of antibody in tissue culture medium for characterization.

The anti-MDL-1 antibody molecules of the present invention may also be produced recombinantly (e.g., in an *E. coli*/T7 expression system as discussed above). In this embodiment, nucleic acids encoding the antibody molecules of the invention (e.g., $V_H$ or $V_L$) may be inserted into a pET-based plasmid and expressed in the *E. coli*/T7 system. There are several methods by which to produce recombinant antibodies which are known in the art. One example of a method for recombinant production of antibodies is disclosed in U.S. Pat. No. 4,816,567 which is herein incorporated by reference. Transformation may be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding fragment thereof, the light chain and/or antigen-binding fragment thereof are introduced into mammalian host cells, the antibodies are produced by culturing the host cells for a period of time sufficient to allow for expression of the antibody in the host cells or, more preferably, 5 secretion of the antibody into the culture medium in which the host cells are grown.

Antibodies may be recovered from the culture medium using standard protein purification methods. Further, expression of antibodies of the invention (or other moieties therefrom) from production cell lines may be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

Antibody fragments, preferably antigen-binding antibody fragments, fall within the scope of the present invention also include F(ab)₂ fragments which may be produced by enzymatic cleavage of an IgG by, for example, pepsin. Fab fragments may be produced by, for example, reduction of F(ab)₂ with dithiothreitol or mercaptoethylamine. A Fab fragment is a $V_L$-$C_L$ chain appended to a $V_H$-$C_{H1}$ chain by a disulfide bridge. A F(ab)₂ fragment is two Fab fragments which, in turn, are appended by two disulfide bridges. The Fab portion of an F(ab)₂ molecule includes a portion of the $F_c$ region between which disulfide bridges are located.

As is well known, Fv, the minimum antibody fragment which contains a complete antigen recognition and binding site, consists of a dimer of one heavy and one light chain variable domain ($V_H$-$V_L$) in non-covalent association. In this configuration that corresponds to the one found in native antibodies the three complementarity determining regions (CDRs) of each variable domain interact to define an antigen binding site on the surface of the $V_H$-$V_L$ dimer. Collectively, the six CDRs confer antigen binding specificity to the antibody. Frameworks (FRs) flanking the CDRs have a tertiary structure that is essentially conserved in native immunoglobulins of species as diverse as human and mouse. These FRs serve to hold the CDRs in their appropriate orientation. The constant domains are not required for binding function, but may aid in stabilizing $V_H$-$V_L$ interaction. Even a single variable domain (or half of an Fv comprising only three CDRs specific for an antigen) has the ability to recognize and bind antigen, although usually at a lower affinity than an entire binding site (Painter, Biochem. 11 (1972), 1327-1337). Hence, said domain of the binding site of the antibody construct as defined and described in the present invention may be a pair of $V_H$-$V_L$, $V_H$-$V_H$ or $V_L$-$V_L$ domains of different immunoglobulins. The order of $V_H$ and $V_L$ domains within the polypeptide chain is not decisive for the present invention, the order of domains given hereinabove may be reversed usually without any loss of function. It is important, however, that the $V_H$ and $V_L$ domains are arranged so that the antigen binding site may properly fold. An $F_V$ fragment is a $V_L$ or $V_H$ region.

Depending on the amino acid sequences of the constant domain of their heavy chains, immunoglobulins may be assigned to different classes. There are at least five major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2.

The anti-MDL-1 antibody molecules or the MDL-1 soluble proteins of the invention may also be conjugated to a chemical moiety. The chemical moiety may be, inter alia, a polymer, a radionuclide or a cytotoxic factor. Preferably the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee et al., (1999) (*Bioconj. Chem.* 10:973-981) discloses PEG conjugated single-chain antibodies. Wen et al., (2001) (*Bioconj.*

Chem. 12:545-553) disclose conjugating antibodies with PEG which is attached to a radiometal chelator (diethylenetriaminpentaacetic acid (DTPA)).

The antibodies and antibody fragments or the MDL-1 soluble proteins or fragments thereof of the invention may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr and $^{56}$Fe.

The antibodies and antibody fragments, the MDL-1 soluble proteins, MDL-1 fusion proteins, or fragments thereof of the invention may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules or soluble MDL-1 proteins may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *momordica charantia* inhibitor, curcin, crotin, *saponaria officinalis* inhibitor, mitogellin, restrictocin, phenomycin, and enomycin.

Any method known in the art for conjugating the antibody molecules or protein molecules of the invention to the various moieties may be employed, including those methods described by Hunter et al., (1962) *Nature* 144:945; David et al., (1974) *Biochemistry* 13:1014; Pain et al., (1981) *J. Immunol. Meth.* 40:219; and Nygren, J., (1982) *Histochem. and Cytochem.* 30:407. Methods for conjugating antibodies and proteins are conventional and very well known in the art.

Antigenic (i.e., immunogenic) fragments of the MDL-1 peptides of the invention are within the scope of the present invention. Antigenic fragments may be joined to other materials, such as fused or covalently joined polypeptides, to be used as immunogens. The antigenic peptides may be useful for preparing antibody molecules which recognize MDL-1 or any fragment thereof. An antigen and its fragments may be fused or covalently linked to a variety of immunogens, such as keyhole limpet hemocyanin, bovine serum albumin, or ovalbumin (Coligan et al. (1994) *Current Protocols in Immunol.*, Vol. 2, 9.3-9.4, John Wiley and Sons, New York, N.Y.). Peptides of suitable antigenicity may be selected from the polypeptide target, using an algorithm, see, e.g., Parker et al. (1986) *Biochemistry* 25:5425-5432; Jameson and Wolf (1988) *Cabios* 4:181-186; Hopp and Woods (1983) *Mol. Immunol.* 20:483-489.

Although it is not always necessary, when MDL-1 peptides are used as antigens to elicit antibody production in an immunologically competent host, smaller antigenic fragments are preferably first rendered more immunogenic by cross-linking or concatenation, or by coupling to an immunogenic carrier molecule (i.e., a macromolecule having the property of independently eliciting an immunological response in a host animal, such as diptheria toxin or tetanus). Cross-linking or conjugation to a carrier molecule may be required because small polypeptide fragments sometimes act as haptens (molecules which are capable of specifically binding to an antibody but incapable of eliciting antibody production, i.e., they are not immunogenic). Conjugation of such fragments to an immunogenic carrier molecule renders them more immunogenic through what is commonly known as the "carrier effect".

Carrier molecules include, e.g., proteins and natural or synthetic polymeric compounds such as polypeptides, polysaccharides, lipopolysaccharides, etc. Protein carrier molecules are especially preferred, including, but not limited to, keyhole limpet hemocyanin and mammalian serum proteins such as human or bovine gammaglobulin, human, bovine or rabbit serum albumin, or methylated or other derivatives of such proteins. Other protein carriers will be apparent to those skilled in the art. Preferably, the protein carrier will be foreign to the host animal in which antibodies against the fragments are to be elicited.

Covalent coupling to the carrier molecule may be achieved using methods well known in the art; the exact choice of which will be dictated by the nature of the carrier molecule used. When the immunogenic carrier molecule is a protein, the fragments of the invention may be coupled, e.g., using water-soluble carbodiimides such as dicyclohexylcarbodiimide or glutaraldehyde.

Coupling agents, such as these, may also be used to crosslink the fragments to themselves without the use of a separate carrier molecule. Such cross-linking into aggregates may also increase immunogenicity. Immunogenicity may also be increased by the use of known adjuvants, alone or in combination with coupling or aggregation.

Adjuvants for the vaccination of animals include, but are not limited to, Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecylammonium bromide, N,N-dioctadecyl-N',N'-bis (2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The polypeptides could also be administered following incorporation into liposomes or other microcarriers.

Information concerning adjuvants and various aspects of immunoassays are disclosed, e.g., in the series by P. Tijssen, *Practice and Theory of Enzyme Immunoassays*, 3rd Edition, 1987, Elsevier, New York. Other useful references covering methods for preparing polyclonal antisera include *Microbiology*, 1969, Hoeber Medical Division, Harper and Row; Landsteiner, *Specificity of Serological Reactions*, 1962, Dover Publications, New York, and Williams, et al., *Methods in Immunology and Immunochemistry*, Vol. 1, 1967, Academic Press, New York.

The anti-MDL-1 "antibody molecules" of the invention include, but are by no means not limited to, anti-MDL-1 antibodies (e.g., monoclonal antibodies, polyclonal antibodies, bispecific antibodies and anti-idiotypic antibodies) and fragments, preferably antigen-binding fragments, thereof, such as Fab antibody fragments, F(ab)$_2$ antibody fragments, Fv antibody fragments (e.g., V$_H$ or V$_L$), single chain Fv antibody fragments and dsFv antibody fragments. Furthermore, the antibody molecules of the invention may be fully human antibodies, mouse antibodies, rabbit antibodies, chicken antibodies, human/mouse chimeric antibodies or humanized antibodies.

The anti-MDL-1 antibody molecules of the invention preferably recognize human or mouse MDL-1 peptides of the invention; however, the present invention includes antibody molecules which recognize MDL-1 peptides from different species, preferably mammals (e.g., non-human primates, pig, rat, rabbit, sheep or dog).

The present invention also includes complexes comprising the MDL=1 peptides of the invention and one or more antibody molecules, e.g., bifunctional antibodies. Such complexes may be made by simply contacting the antibody molecule with its cognate peptide.

Various methods may be used to make the antibody molecules of the invention. In preferred embodiments, the antibodies of the invention are produced by methods which are similar to those disclosed in U.S. Pat. Nos. 5,625,126; 5,877,397; 6,255,458; 6,023,010 and 5,874,299. Hybridoma cells which produce monoclonal, fully human anti-MDL-1 peptide antibodies may then be produced by methods which are commonly known in the art. These methods include, but are not limited to, the hybridoma technique originally developed by Kohler et al., (1975) (*Nature* 256:495-497), as well as the trioma technique (Hering et al., (1988) *Biomed. Biochim. Acta.* 47:211-216 and Hagiwara et al., (1993) *Hum. Antibod. Hybridomas* 4:15), the human B-cell hybridoma technique (Kozbor et al., (1983) *Immunology Today* 4:72 and Cote et al., (1983) *Proc. Natl. Acad. Sci. U.S.A.* 80:2026-2030), and the EBV-hybridoma technique (Cole et al., in *Monoclonal Antibodies and Cancer Therapy*, Alan R. Liss, Inc., pp. 77-96, 1985). Again, ELISA may be used to determine if hybridoma cells are expressing anti-MDL-1 peptide antibodies.

Purification of antigen is not necessary for the generation of antibodies. Immunization may be performed by DNA vector immunization, see, e.g., Wang, et al. (1997) *Virology* 228:278-284. Alternatively, animals may be immunized with cells bearing the antigen of interest. Splenocytes may then be isolated from the immunized animals, and the splenocytes may be fused with a myeloma cell line to produce a hybridoma (Meyaard et al. (1997) *Immunity* 7:283-290; Wright et al. (2000) *Immunity* 13:233-242; Preston et al. (1997) *Eur. J. Immunol.* 27:1911-1918). Resultant hybridomas may be screened for production of the desired antibody by functional assays or biological assays, that is, assays not dependent on possession of the purified antigen. Immunization with cells may prove superior for antibody generation than immunization with purified antigen (Kaithamana et al. (1999) *J. Immunol.* 163:5157-5164).

Antibody to antigen and ligand to receptor binding properties may be measured, e.g., by surface plasmon resonance (Karlsson et al. (1991) *J. Immunol. Methods* 145:229-240; Neri et al. (1997) *Nat. Biotechnol.* 15:1271-1275; Jonsson et al. (1991) *Biotechniques* 11:620-627) or by competition ELISA (Friguet et al. (1985) *J. Immunol. Methods* 77:305-319; Hubble (1997) *Immunol. Today* 18:305-306). Antibodies may be used for affinity purification to isolate the antibody's target antigen and associated bound proteins, see, e.g., Wilchek et al. (1984) *Meth. Enzymol.* 104:3-55.

Antibodies that specifically bind to variants of MDL-1, where the variant has substantially the same nucleic acid and amino acid sequence as those recited herein, but possessing substitutions that do not substantially affect the functional aspects of the nucleic acid or amino acid sequence, are within the definition of the contemplated methods. Variants with truncations, deletions, additions, and substitutions of regions which do not substantially change the biological functions of these nucleic acids and polypeptides are within the definition of the contemplated methods.

Bispecific antibodies are antibodies that have binding specificities for at least two different epitopes. Exemplary bispecific antibodies may bind to two different epitopes of MDL-1L. Alternatively, bispecific MDL-1 antibodies can bind to another antigen, e.g., DC-SIGN, CD20, RANK-L, etc.

Methods for making bispecific antibodies are known in the art. Traditional production of full-length bispecific antibodies is based on the co-expression of two immunoglobulin heavy-chain-light-chain pairs, where the two chains have different specificities (Millstein et al. *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al. *EMBO J,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding, present in at least one of the fusions. DNAs encoding the immunoglobulin heavy-chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy-chain-light-chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al. *Methods in Enzymology,* 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al. *Science,* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli,* which can be chemically coupled to form bispecific antibodies. Shalaby et al. (1992) *J. Exp. Med.,* 175:217-225 describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al. (1992) *J. Immunol.,* 148(5):1547-1553. The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al. (1993) *Proc. Natl. Acad. Sci. USA,* 90:6444-6448 has provided an alternative mechanism for making bispecific antibody fragments. The fragments comprise a heavy-chain variable domain (V$_H$) connected to a light-chain variable domain (V$_L$) by a linker which is too short to allow pairing between the two domains on the same chain. Accordingly, the V$_H$ and V$_L$ domains of one fragment are forced to pair with the complementary V$_L$ and V$_H$ domains of another fragment, thereby forming two antigen-binding sites. Another strategy for making bispecific antibody fragments by the use of single-chain Fv (sFv) dimers has also been reported. See Gruber et al. (1994) *J. Immunol.,* 152:5368.

Antibodies with more than two valencies are contemplated. For example, trispecific antibodies can be prepared. Tutt et al. (1991) *J. Immunol.* 147: 60.

Uses

The invention provides methods for the screening of compounds that modulate the Gal9/MDL-1 interaction and antagonize receptor signaling or function. The methods may comprise the screening of a binding composition specific for a polypeptide or nucleic acid of MDL-1, e.g., an antibody or antigen binding fragment thereof. Control binding compositions are also provided, e.g., control antibodies, see, e.g., Lacey et al. (2003) *Arthritis Rheum.* 48:103-109; Choy and Panayi (2001) *New Engl. J. Med.* 344:907-916; Greaves and Weinstein (1995) *New Engl. J. Med.* 332:581-588; Robert and Kupper (1999) *New Engl. J. Med.* 341:1817-1828; Lebwohl (2003) *Lancet* 361:1197-1204.

Phosphorylation assays are contemplated to screen for compounds that modulate the interaction of Gal9 and MDL-1. For cell based phosporylation assays, myeloid cells expressing MDL-1 are combined with T cells known to express Tim3 or other proteins that bind Gal9. When Gal9 and MDL-1 interact, tyrosine phosphorylation of the MDL-1 signaling partner, DAP12 takes place. A compound of interest is added to the T cell and myeloid cell mixture. Lysates are prepared and samples are analyzed for the ability of test compounds to increase or decrease phosphorylation.

Phosphorylation can be analyzed by several means including immunoprecipation followed by immunoblotting, ELISA, cell based ELISA, flow cytometry, immunocytochemistry (ICC), immunohistochemistry (IHC; see, e.g., Zell, T. et al. (2001) *Proc. Natl. Acad. Sci. USA* 98:10805; and Willinger, T. et al. (2005) *J. Immunol.* 175:5895), and immobilized metal affinity chromatography (IMAC; see, e.g., Brill, L. M. et al. (2004) *Anal. Chem.* 76:2763). Alternatively Gal9 binding to MDL-1 can be assessed using an surface plasmon resonance optical biosensor, such as Biacore (see, e.g., Leonard, et al. (2011) *Meth. Mol. Bio.* 681:403-418).

The invention also provides a kit comprising a cell and a compartment, a kit comprising a cell and a reagent, a kit comprising a cell and instructions for use or disposal, as well as a kit comprising a cell, compartment, and a reagent.

The broad scope of this invention is best understood with reference to the following examples, which are not intended to limit the inventions to the specific embodiments.

Examples

I. General Methods

Some of the standard methods are described or referenced, e.g., in Maniatis, et al. (1982) *Molecular Cloning, A Laboratory Manual,* Cold Spring Harbor Laboratory, Cold Spring Harbor Press; Sambrook, et al. (1989) *Molecular Cloning: A Laboratory Manual,* (2d ed.), vols. 1-3, CSH Press, NY; Ausubel, et al., *Biology,* Greene Publishing Associates, Brooklyn, N.Y.; or Ausubel, et al. (1987 and Supplements) *Current Protocols in Molecular Biology,* Greene/Wiley, New York. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in Meth. Enzymol., vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1990) "Purification of Recombinant Proteins with Metal Chelate Absorbent" in Setlow (ed.) *Genetic Engineering, Principle and Methods* 12:87-98, Plenum Press, N.Y.; and Crowe, et al. (1992)

*QIAexpress: The High Level Expression & Protein Purification System,* Qiagen, Inc., Chatsworth, Calif.

Computer sequence analysis is performed, e.g., using available software programs, including those from the GCG (U. Wisconsin) and GenBank sources. Public sequence databases were also used, e.g., from GenBank and others.

II. Gal9-MDL-1 Pull-Down Assay

A pulldown assay employed Invitrogen's M-270 Epoxy Dynabeads bound to MDL-1-Ig or Control-Ig. Beads were incubated for 45 minutes at 4° C. with lysates from fresh bone marrow derived stromal cell line, ST-2. Samples were analyzed by nano-liquid chromatography tandem mass spectrometry on the LTQ-Orbitrap to determine unique protein sequences. Galectin-9 was revealed as a key protein which linked specifically with MDL-1 Ig fusion protein.

III. Tyrosine Phosphorylation of DAP12

Cell lysates were prepared from MCSF differentiated human macrophages that were stimulated with galectin-9, galectin-4, galectin-8, anti-MDL-1 (DX246; agonist antibody) or control Ig for 5-15 minutes at 37° C. Lysates were immunoprecipitated with anti-MDL-1 antibody.

Samples were analyzed by western blotting for the presence of tyrosine phosphorylated proteins. Gal9 and DX246 stimulation resulted in DAP12 phosphorylation. The blot was stripped and reprobed with anti-Dap12 antibody to confirm the specificity of the phosphorylated protein bands. Samples were also analyzed for the amount of MDL-1 present in each treatment sample.

III. Human Osteoclastogenesis Assays

Galectin-9 promotes RankL-independent in vitro differentiation of giant cells and osteoclast-like cells in human peripheral blood CD14+ monocytes cultured in medium containing 30 ng/ml human recombinant M-CSF for 7 days, in the same manner and with the same kinetics as MDL-1 agonistic antibodies.

CD14+ cells were enriched using RosetteSep Human Monocyte Enrichment Cocktail kit and method. Monocytes were cultured in RPMI-10 complete medium containing 30 ng/ml R&D rhM-CSF for 7 days. Cells were diluted to 0.4× 106 cell/ml in RPMI complete+M-CSF, plated and cultured on 8-well chambered coverslides for 24 hours. Cells were stimulated the next day with either 1) recombinant human Gal9 (rhGal9; 10 mg/mL), 2) anti-MDL-1 agonist mAb (DX163; 10 mg/ml), 3) or an isotype control mAb (msIgG1; 10 mg/ml). The cells were stimulated for 2-3 days and then stained for analysis and photomicrograph recording. Giant cells and osteoclast-like cells were stained in HEMA3 and then with methanoloic Phalloidin-AF594 for F-Actin immunofluorescence stain. Images were recorded on a Nikon Eclipse E600 microscope using a Nuance Fx CRi imaging system.

Both the MDL-1 agonist antibody, DX163, and rhGal9 treatment resulted in the formation of osteoclast-like cells. Thus, engagement of Gal9 with MDL-1 expressed on myeloid lineage cells induces MDL-1 activity similar to the stimulation by an agonist antibody.

IV. Gal9 Exacerbates Disease in an Murine Antibody Induced Arthritis (AIA) Model B10.RIII male mice were induced with 3 mg of arthrogen-CIA antibody cocktail (from Chondrex) on day 0. Three groups (n=4) were treated on day 2: 1) naïve, 2) control-Ig (50 µg), or 3) mouse Galectin-9 (from GalPharma). Arthritic disease progression was monitored for 7 days.

Gal9 treatment resulted in a significant increase of disease progression over both the naïve and control-Ig treatment groups (see FIG. 1). Further gene expression studies from the treatment groups showed that Gal9 induced upregulation of inflammatory, bone remodeling and tissue-homing chemokine expression.

V. Treatment with MDL-1-Ig Fusion Protein Inhibited IL-23-Induced Enthesopathy

B10.RIII mice were injected with 3 µg of minicircle plasmid DNA containing IL-23 gene sequence at day 0. Transgene-induced expression of IL-23 promoted joint inflammation beginning on day 5. On the day of disease onset, mice were treated with 1.0 mg of MDL-1-Ig fusion protein. As seen in FIG. 1, the MDL-1 fusion protein inhibited the interaction between MDL-1 positive macrophages and MDL-1L positive cells. Mice were treated with additional MDL-1-Ig (0.5 mg/dose) at day 10 and 15. n=5 mice per group.

IL-23 promotes enthesopathy by activating IL-23R+ CD45+ Thy1+ immune cells. This result indicates the MDL-1 may be interact directly or indirectly with CD45+ Thy1+ cells. The data represented by FIG. 1 indicates that targeting these cells with an MDL-1 fusion protein will suppress IL-23-dependent inflammatory disorders.

VI. MDL-1 Tetramers Staining of Lymph Node Cells Identified a Population of T Lymphocytes that Interact with MDL-1

PE labeled tetrameric MDL-1 proteins were generated to detect cell surface interaction with T lymphocytes by flow cytometry. Recombinant murine MDL-1-Ig fusion protein was manufactured in-house engineered with a BirA (biotin-ligase) targeting site The MDL-1-Ig protein stock was desalted using Zeba Spin™ desalting columns 7 kDa MWCO (Pierce) according to the manufacturer's protocol. During the desalting procedure, the MDL-1-Ig protein buffer was exchanged for a low-salt biotinylation buffer (10 mM Tris-HCl, 7.5 mM MgCl$_2$, 5.0 mM NaCl, pH 8.0). Next, 500 µg aliquots of MDL-1-Ig were biotinylated using BirA biotin-ligase (Avidity) according to the manufacturer's protocol for 1 hour at 30° C. The biotinylation reaction was subsequently transferred to a Slide-A-Lyzer™ dialysis cassette, 10 kDa MWCO (Pierce). The protein was dialyzed overnight in 2 L DPBS at 4° C. to remove excess free biotin. The dialyzed MDL-1-Ig-biotin sample was then concentrated using Vivaspin™ 500 10 kDa MWCO (GE Healthcare) and quantified using the BCA assay (Thermo). 200 µg of MDL-1-Ig-biotin was aliquoted into a microfuge tube for tetramerization. 25 µg of premium grade Streptavidin-PE (Invitrogen) was added to the MDL-1-Ig-biotin sample 10 times. After each addition of Streptavidin-PE, the sample was incubated for 10 minutes at room temperature. Following quality analysis by mass spectrometry, tetramerized MDL-1-Ig was stored in the dark at 4° C.

Figure 2:
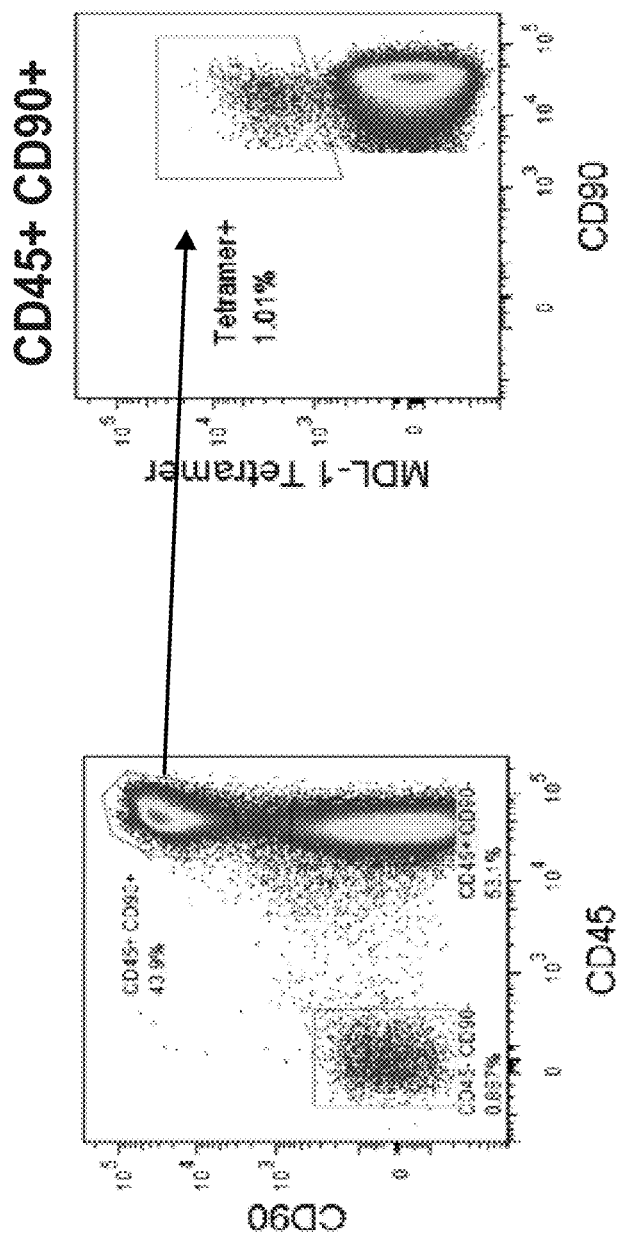
FIG. 2 shows that MDL-1-Ig tetramer staining of lymphocytes.

Lymph node cells were isolated from naïve B10.RIII mice. Cells were first stained with a vital dye, Fcγ receptors (FcγRs) were blocked with FCγR specific antibodies, and the cells were subsequently stained with fluorochrome-labeled anti-CD45 and anti-CD90 mAbs. The results represented by FIG. 2 showed that about 1% of CD45+, CD90+ lymphoid cells were positive for MDL-1 tetramer staining CD90 negative myeloid cells were negative for MDL-1 tetramer staining.

VII. MDL-1-Ig Staining Confirmed CD45, CD90, and CD117 Expression on T Lymphocytes that Interact with MDL-1

Bone marrow was harvested from naïve, wildtype B10.RIII mice. Samples were first stained with a viability dye, then FcγRs were blocked with antibodies. The Zenon Mouse™ IgG labeling kit (Invitrogen, Cat# Z25152) was used to label MDL-1-Ig reagent with biotin. Bone marrow samples were then either left unstained, or were stained with 5 mg of MDL-1-Ig-Biotin. Lastly, all samples were stained with antibodies against CD45, CD90 (Thy1), CD117 (c-kit), as well as with Streptavidin-PE. Bone marrow samples were acquired on the BD LSRII flow cytometer and were analyzed using TreeStar's FlowJo software.

Figure 3:
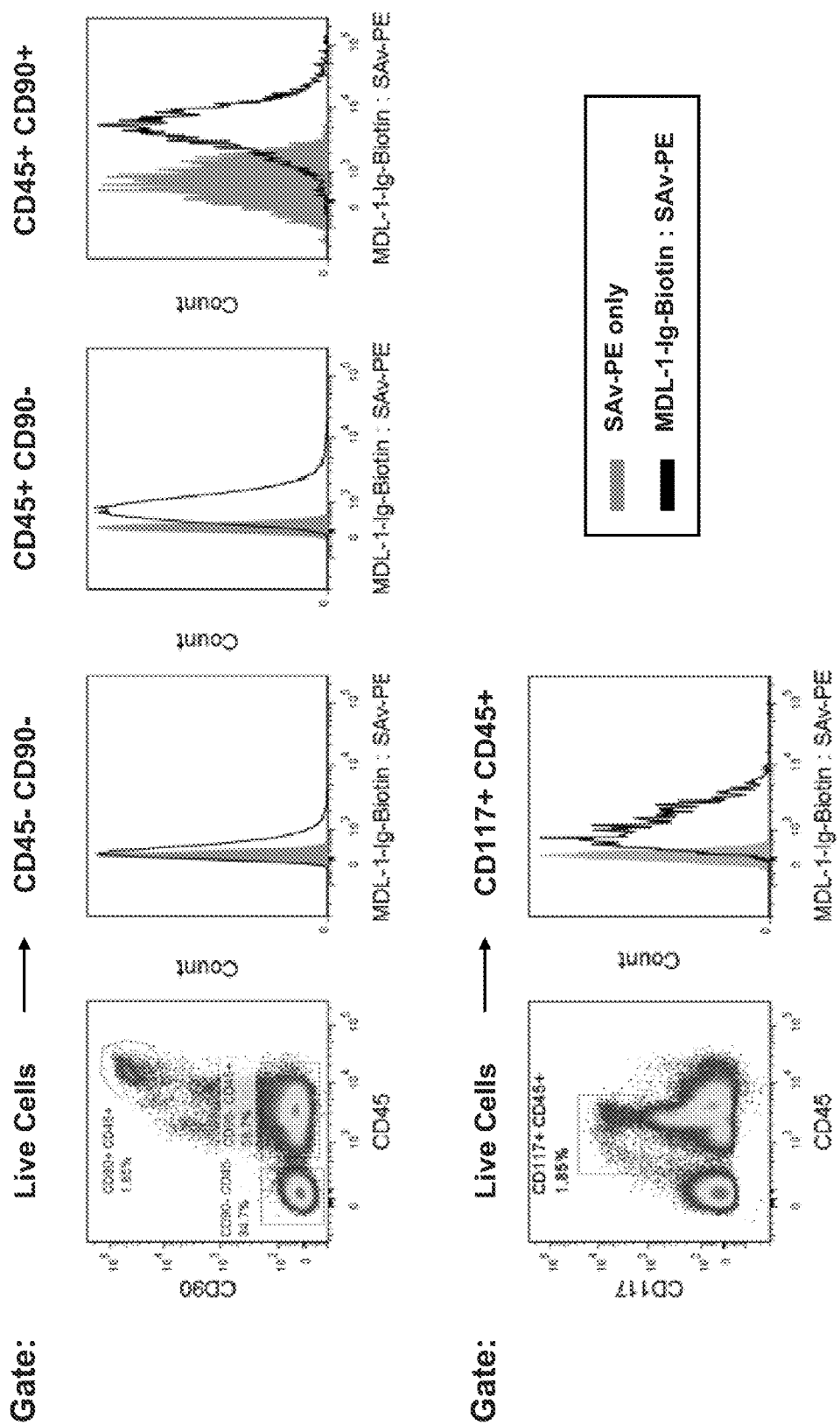
FIG. 3 shows MDL-1-Ig staining of CD45$^+$, CD90$^+$, and CD117$^+$ lymphocytes.
Figure 4:
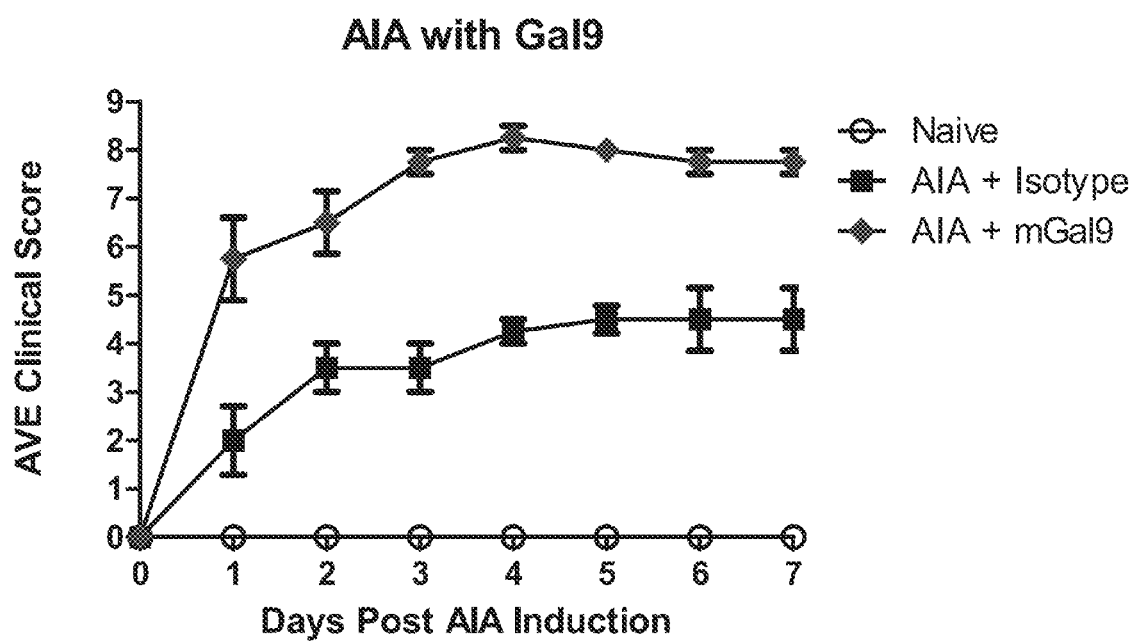
FIG. 4 shows Gal9 treatment exacerbates disease in a murine antibody-induced arthritis model.

For analysis, bone marrow cells were gated first on size, then on viability to exclude dead cells. The results represented by FIG. 3 showed that live cells were further gated on subsets according to CD90 and CD45 expression and subsets were then analyzed for background staining or MDL-1-Ig staining CD117+CD45+ cells were also gated from live cells, and were analyzed for background and MDL1-Ig staining as before.

These results indicate that MDL-1L is expressed on a population of T lymphocytes that also express CD45, CD90, and CD117.

VIII. Depletion of T Lymphocyte Population with MDL-1 Fusion Protein

An MDL-1-Ig fusion protein, specifically, an MDL-1-Ig is used for in vitro and in vivo depletetion of the T lymphocyte population expressing CD45, CD90, CD117, and IL-23R. To increase antibody dependent cellular cytoxicity ("ADCC"), the Fc portion of the MDL-1-Ig protein is a-fucosylated as described, e.g., in Sheilds et al. (2002) *J. Biol. Chem.* 277: 26733-26740. Depletion of the T lymphocyte population is analyzed using standard fluorescent activated cell sorting (FACS) techniques.

What is claimed is:

1. A method of depleting a population of T lymphocyte cells comprising contacting the population of T lymphocyte cells with an MDL-1 fusion protein that binds directly or indirectly to a molecule expressed on the T lymphocyte cells wherein the MDL-1 fusion protein comprises an extracellular domain of MDL-1 and a heterologous protein which is an Fc portion of an immunoglobulin molecule.

2. The method of claim 1, wherein the heterologous protein is human serum albumin.

3. The method of claim 1, wherein the population of T lymphocyte cells express CD45, CD90, and CD117.

4. The method of claim 3, wherein the population of T lymphocyte cells further express IL-23R.

5. The method of claim 4, wherein the population of T lymphocyte cells mediate enthesopathy.

* * * * *